United States Patent [19]
Lee et al.

[11] Patent Number: 5,994,412
[45] Date of Patent: Nov. 30, 1999

[54] BIS-ARYL ETHERS, COMPOSITIONS CONTAINING SUCH COMPOUNDS AND METHODS OF TREATMENT

[75] Inventors: Seok H. Lee, Seoul, Rep. of Korea; Maria T. Diez, Madrid, Spain; Fernando Pelaez, Madrid, Spain; Marina Mojena Sanchez, Madrid, Spain; M. Dolores Vilella Amils, Madrid, Spain; Hans E. Huber, Lansdale; Denis R. Patrick, Chalfont, both of Pa.; Otto D. Hensens, Red Bank, N.J.; Rosalind G. Jenkins, Somerset, N.J.; Leeyuan Huang, Watchung, N.J.; Annie Z. Zhao, Edison, N.J.; Deborah L. Zink, Manalapan, N.J.; Anne Dombrowski, East Brunswick, N.J.; Gerald F. Bills, Clark, N.J.

[73] Assignee: Merck & Co., Inc., Rahway, N.J.

[21] Appl. No.: 09/110,006

[22] Filed: Jul. 2, 1998

Related U.S. Application Data

[60] Provisional application No. 60/052,163, Jul. 10, 1997.

[51] Int. Cl.⁶ .................................................. A01N 31/14
[52] U.S. Cl. .......................... 514/721; 568/637; 435/156
[58] Field of Search .............................. 568/637; 514/721

[56] References Cited

PUBLICATIONS

Barton J chem Soc 1958 p. 1767, 1958.
Hassal Jchem Soc 1959 p. 2831, 1959.
Daum, G. et al., "The ins and outs of Raf kinases," Trends Biochem, Sci., 19, pp. 474–480 (1994).
Kizaka–Kondoh, S. et al., "Raf–1 Protein Kinase Is an Integral Component of the Oncogenic Signal Cascade Shared by Epidermal Growth Factor and Platelet–Derived Growth Factor," Mol. and Cellular Biol., vol. 12, No. 11, pp. 5078–5086 (1992).

Marshall, M., "Interactions Between Ras and Raf: Key Regulatory Proteins in Cellular Transformation," Molecular Reproduction and Development, vol. 42, pp. 493–499 (1995).
Schaap, D. et al., "A Dominant–negative Mutant of raf Blocks Mitogen–activated Protein Kinase Activation by Growth Factors and Oncogenic p21ras*," The Jour. of Biol. Chem., vol. 268, No. 27, pp. 20232–20236 (1993).
White, M. A. et al., "Multiple Ras Functions Can Contribute to Mammalian Cell Transformation," Cell, vol. 80, pp. 533–541 (1995).
Williams, N.G. and Roberts, T.M., "Signal transduction pathways involving the Raf proto–oncogene," Cancer and Metastasis Reviews, vol. 13, No. 1, pp. 105–116 (1994).

*Primary Examiner*—Robert Gerstl
*Attorney, Agent, or Firm*—Dianne Pecoraro; Mark R. Daniel

[57] ABSTRACT

A compound represented by the formula I is disclosed:

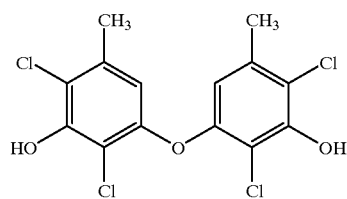

or a pharmaceutically acceptable salt or hydrate thereof. The compound has inhibitory activity against the oncoprotein Raf.

Also included are pharmaceutical compositions, methods of treating cancer, cultures of the producing fungal microorganism and methods of fermentative production of the compound.

6 Claims, No Drawings

BIS-ARYL ETHERS, COMPOSITIONS CONTAINING SUCH COMPOUNDS AND METHODS OF TREATMENT

This application claims benefit of Provisional Appl. 60/052,163 filed Jul. 10, 1997.

BACKGROUND OF THE INVENTION

The present invention relates to bis-aryl ethers having anti-cancer activity, compositions containing such compounds and methods of use. Additionally, the compounds are derived from a fungal culture which is included in the present invention. The organism is described herein as well as culture techniques useful for the production of the microorganism and the compound.

The method of treating cancer which is described herein relates to cancers which are effected by raf and raf-inducible genes and proteins. The cancers which can be treated are primarily Raf mediated tumors. Raf, and in particular, c-raf, is an oncogene which is overexpressed in a wide variety of tumors.

The raf genes code for a family of proteins which can be oncogenically activated through N-terminal fusion, truncation or point mutations. Raf undergoes rapid phosphorylation in response to PDGF, EGF, insulin, thrombin, endothelin, acidic FGF, CSF1 or TPA, as well as in response to oncoproteins v-fms, v-src, v-sis, Hras and polyoma middle T antigen. The raf family of oncogenes encompasses human A-raf-1, B-raf-1 and C-raf-1. The A-raf-1 gene is located on chromosome Xp11.3 and is expressed in numerous tissues and tissue types. It encodes a cytosolic protein of approximately 68,000 daltons. The C-raf-1 gene is located on chromosome 3p25 in a chromosomal site that has been found to be altered in several epithelial cancers. The gene encodes a protein which is approximately 74,000 daltons.

There is evidence that raf genes function downstream of ras in the transduction of activation signals from the membrane to the nucleus. By inhibiting raf as described herein, diseases in which ras, raf and other oncogenes integral to the transduction pathway can be treated.

Antisense constructs which reduce cellular levels of c-Raf, and hence Raf activity, inhibit the growth of oncogene-transformed rodent fibroblasts in soft agar, while exhibiting little or no general cytotoxicity. Since inhibition of growth in soft agar is highly predictive of tumor responsiveness in whole animals, these studies suggest that the antagonism of Raf is an effective means by which to treat cancers in which Raf plays a role.

Additionally, antisense Raf oligonucleotides are efficacious in nude mouse xenograft studies in vivo, further validating Raf as a target which can be inhibited to treat cancer. Monia, B. P., et al. Nature Medicine 2(6): 668–675 (1996).

Examples of cancers where Raf is implicated through overexpression, include cancers of the brain, genitourinary tract, lymphatic system, stomach, larynx and lung. These include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma.

SUMMARY OF THE INVENTION

A compound represented by formula I is disclosed:

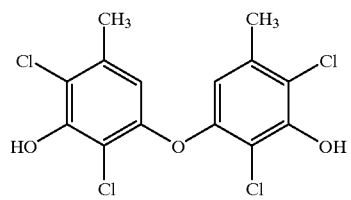

I as well as pharmaceutically acceptable salts and hydrates thereof.

Also included is a pharmaceutical composition which is comprised of a compound of formula I or a pharmaceutically acceptable salt or hydrate thereof in combination with a carrier.

Also included is a method of treating cancer in a mammalian patient in need of such treatment which is comprised of admininstering to said patient an anti-cancer effective amount of a compound of formula I or a pharmaceutically acceptable salt or hydrate thereof.

Also included is a substantially pure culture of a fungal microorganism which produces a compound of formula I or a pharmaceutically acceptable salt or hydrate thereof.

More particularly, a substantially pure culture of the organism Chaetophoma sp. is included herein.

Even more particularly, a substantially pure culture of the organism described in accordance with ATCC No. 74405 is included.

Also included is a process for producing a compound of formula I, or a salt or hydrate thereof, which comprises aerobically cultivating a culture of ATCC No. 74405 in a nutrient medium containing assimilable sources of carbon and nitrogen and isolating said compound therefrom.

These and other aspects of the invention will be apparent from the teachings contained herein.

DETAILED DESCRIPTION OF THE INVENTION

A compound represented by the formula I is disclosed:

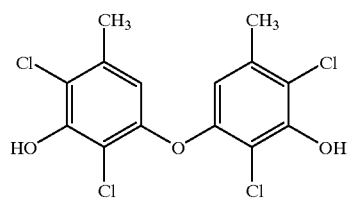

I as well as pharmaceutically acceptable salts and hydrates thereof.

The compound of formula I can be derived from a culture of the fungal organism Chaetophoma sp. which is described below.

ISOLATION AND CHARACTERIZATION OF FUNGUS

The producing fungus, Chaetophoma sp., (ATCC No. 74405) was isolated from the thallus of a foliose lichen, collected near Playa La Parguera, Puerto Rico.

In agar culture, colonies of the fungus exhibit the following morphology:

Colonies on oatmeal agar (Difco) at 23° C., 12 hr photoperiod, growing very slowly, attaining 45–48 mm in 21 days, with margin raised, even, with aerial mycelium velvety to wooly, with some radial folding or buckling of the medium, pale gray to dull browish gray, Pallid Neutral Gray, Pallid Mouse Gray, Light Neutral Gray, Neutral Gray, Mouse Gray, Deep Mouse Gray, Dark Mouse Gray (capitalized color names from Ridgway, R. 1912), with reverse dull gray, brown to blackish brown, exudates clear to pale brown, odors absent.

Colonies on YME agar (D-glucose 4 g, malt extract 10 g, yeast extract 2 g, $H_2O$ 1 liter agar 20 g) at 23 C, 12 hr photoperiod, growing slowly, attaining 41–43 mm in 21 days, submerged to appressed at the margin, raised towards the center, with velvety to wooly aerial mycelium, zonate, pale grayish brown to yellow brown, gray, to dull olive brown, Drab, Old Gold, Hair Brown, Deep Olive-Buff, Dark Olive-Buff, olivaceous brown to grayish brown in reverse, exudate clear to golden brown, odors absent. No growth at 37° C.

Colonies on LCA agar (D-glucose 1.0 g, carboxymethyl cellulose 1.0 g, $KH_2PO_4$ 1.0 g, $MgSO_4.7H_2O$, KCl 0.2 g, $NaNO_3$ 2 g, yeast extract 0.2 g, agar 13 g, $H_2O$ 1 liter) at 23° C., 12 hr photoperiod attaining 36–37 mm in 21 days, with margin submerged, fimbriate to irregularly undulating, appressed to silky to plumose, granular towards center due development of conidiomata on aerial mycelium, translucent to olive or olive brown, Deep Grayish Olive, Dark Grayish Olive, reverse similar in color. Exudates and odors absent. No growth at 37° C.

Conidiomata pycnidial, up to 250 μm in diameter, subgloblose to pyriform, papillate or not, dehiscing by irregular ostiole in age, solitary to confluent, dark brown to black, shiny, submerged in the agar, at agar surface or on aerial mycelium. Conidomata wall a textura intricata to textura angularis, composed of densely interwoven hyphae and dark irregular plate-like cells, often with adhering vegetative hyphae. Conidiogenous enteroblastic, phialidic, cylindrical or tapered towards apex, straight or curved, often with a slighty flared collarette, with periclinal thickenings sometimes evident at conidiogenous locus, up to 12 μm long×3 μm wide, arising directly from a pseudoparenchymatous layer lining the conidiomatal cavity. Conidia minute, 2–3 μm×1–2 μm, ellipsoidal, cylindrical to nearly allantoid, hyaline, smooth, aseptate, germinating on various agar media at room temperate within 24 hrs, cream-colored in mass. Chlamydospores not observed. Mycelium composed of highly branched, simple septate, hyaline to dematiaceous hyphae characteristic of many ascomycetous fungi.

Following the classification scheme of Sutton (Sutton, B. C. 1980. The Coelomycetes. Commonwealth Mycological Institute, Kew. U.K.), the fungus is assigned to the form genus Chaetophoma based on the following set of characteristics: minute pycnidial conidiomata; conidomata with an irregular ostiole; cylindrical, phialidic conidiogenous cells; and minute, hyaline, aseptate conidia.

Thus included in the present invention is a substantially pure culture of a fungal microorganism which produces a compound of formula I or a pharmaceutically acceptable salt or hydrate thereof.

More particularly, a substantially pure culture of the organism Chaetophoma sp. is included herein.

Even more particularly, a substantially pure culture of the fungal organism deposited as ATCC No. 74405 is included herein.

Also included is a process for producing a compound of formula I which comprises aerobically cultivating a culture of ATCC No. 74405 in a nutrient medium containing assimilable sources of carbon and nitrogen and isolating said compound therefrom.

ATCC Deposit No. 74405

Before the U.S. filing date of the present application, a sample of the fungus was deposited at the American Type Culture Collection (ATCC), 12301 Parklawn Drive, Rockville, Md. 20852. The culture access designation is 74405. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

FERMENTATION, PRODUCTION AND ISOLATION

In general, the fungal organism is cultured on a solid medium, or in an aqueous nutrient medium containing sources of assimilable carbon and nitrogen. For example, the cultures can be grown under submerged aerobic conditions (e.g., shaking culture, submerged culture, etc.). The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, dextrin, and the like. Other sources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, polyglycol, mineral oil or silicone may be added.

As to the conditions for the production of the fungus in massive amounts, submerged aerobic cultural conditions is one method of culturing the cells. For the production in small amounts, a shaking or surface culture in a flask or bottle can be employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium can be adjusted to about 6–7 prior to the autoclaving step.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably about 22–25° C., for a period of about 7–28 days, which may be varied according to fermentation conditions and scales.

In particular, the Chaetophoma sp. culture was maintained in sterile soil and stored at 4° C. until ready for use.

The seed culture was inoculated by aseptically transferring a small amount of preserved soil into a 250 ml Erlenmeyer flask containing 50 ml seed medium of the following seed composition.

| Component | (g/liter) |
|---|---|
| Seed Medium | |
| corn steep powder | 2.5 |
| tomato paste | 40.0 |
| oat flour | 10.0 |
| glucose | 10.0 |
| agar | 4.0 |
| trace elements solution | 10 ml/liter |
| Trace Elements Solution | |
| $FeSO_4.7H_2O$ | 1.0 |
| $MnSO_4.4H_2O$ | 1.0 |
| $CuCl_2.2H_2O$ | 0.025 |
| $CaCl_2.2H_2O$ | 0.1 |
| $H_3BO_3$ | 0.056 |
| $(NH_4)_6MoO_{24}.4H_2O$ | 0.019 |
| $ZnSO_4.7H_2O$ | 0.2 |
| | dissolved in 0.6N HCl |

The seed medium was prepared with distilled water, and the pH can be adjusted to 6.8 by adding NaOH. The medium was dispensed into 250 ml Erlenmeyer flasks and capped with cotton plugs before being autoclaved at 121° C. for 20 minutes. The seed culture was incubated at 25° C. on a gyratory shaker (220 rpm, 5.1 cm throw) for approximately 3 days for the formation of biomass. This seed could be used to inoculate the production medium.

The production medium was formulated as follows: millet, 15.0 g/flask and 10.0 ml/flask base liquid (in g/liter of distilled water): yeast extract, 50.0; monosodium glutamate, 10.0; sodium tartrate, 10.0; $FeSO_4.7H_2O$, 1.0 and corn oil, 10.0 ml. The medium was dispensed into 250 ml Erlenmeyer flasks and capped with cotton plugs before being autoclaved at 121° C. for 20 minutes. Just before use, 15 ml water was added to each flask and the flasks resterilized for 20 minutes. Fermentation flasks were inoculated with 2.0 ml vegetative seed growth and were incubated at 25° C., 85% humidity for 35 days without agitation. Each fermentation flask was extracted with 40.0 ml methanol, growth broken up and shaken for 30 minutes. The flasks were pooled and delivered frozen for the isolation of the compound of formula I.

Melted frozen broth or whole broth is extracted twice with methanol (1:1 v/v). The pooled extract is then filtered through a Buchner filter layered with a filter paper and the filter cake is washed with small portions of fresh methanol. The filtrates are then pooled and the solvents removed in vacuo.

Crude extract is partitioned among solvents (dichloromethane, methanol and water). Reverse phase flash column chromatography on a Bakerbond C18 (50×600) Ace glass column is run on the methanol fraction using water/methanol (stepwise gradient). The active fraction is subjected to reverse phase HPLC on Zorbax RX C8 (21.2×25; DuPont) using 40% $CH_3CN$—$H_2O$ (flow rate 10 ml/min) to produce the compound of formula I.

NMR Data

The $^1H$ and $^{13}C$ NMR data for compound I were acquired at ambient temperature and referenced to the solvent peak ($CD_3OD$) at $\delta 3.30$ and 49.0 ppm downfield of TMS, respectively, and are as follows:

$^1H$ NMR ($CD_3OD$, 400 MHz): $\delta 2.25$, (3$\underline{H}$, d, J=0.4Hz), 6.35 (1$\underline{H}$, q, J=0.4 Hz).

13C NMR ($CD_3OD$, 75 Mhz): 20.4, 112.1, 112.6, 118.6, 137.0, 152.0, 152.2 ppm.

As used herein the terms "pharmaceutically acceptable salts" and "hydrates" refer to those salts and hydrated forms of the compound which would be apparent to the pharmaceutical chemist, i.e., those which are substantially nontoxic, or which may favorably affect the pharmacokinetic properties of said compounds, such as palatability, absorption, distribution, metabolism and excretion. Other factors, more practical in nature, which are also important in the selection, are the cost of the raw materials, ease of crystallization, yield, stability, solubility, hygroscopicity and flowability of the resulting bulk drug.

When the compound is charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc.

Pharmaceutically acceptable salts also include acid addition salts. Thus, the compound can be used in the form of salts derived from inorganic or organic acids. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The compound of the invention can be formulated in a pharmaceutical composition by combining the compound with a carrier. Examples of such compositions and carriers are set forth below.

The compound may be employed in powder or crystalline form, in liquid solution, or in suspension. They may be administered by a variety of means; those of principal interest include: orally, parenterally (intravenously or intramuscularly), topically, transdermally and by inhalation.

If a solid carrier is used, the preparation can be tableted, placed in a hard gelatin capsule in powder or pellet form or in the form of a troche or lozenge. The amount of solid carrier will vary widely, but preferably will be from about 0.25 mg to about 1 g. When a liquid carrier is used, the preparation will be in the form of a syrup, emulsion, soft gelatin capsule, sterile injectable liquid such as an ampule or nonaqueous liquid suspension.

Compositions for injection may be prepared in unit dosage form in ampules or in multidose containers. The injectable compositions may take such forms as suspensions, solutions or emulsions, in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

The pharmaceutical carrier employed may be, for example, either a solid or liquid. Examplary of solid carriers are lactose, terra alba, sucrose, talc, gelatin, agar, pectin, acacia, magnesium stearate, stearic acid, and the like. Examplary of liquid carriers are syrup, peanut oil, olive oil, water, and the like. Similarly, the carrier or diluent may include time delay material well known in the art, such as glyceryl mono-stearate or glyceryl distearate alone or with a wax. Topical applications may be formulated in carriers such as hydrophobic or hydrophilic bases to form ointments, creams, lotions, in aqueous, oleaginous or alcoholic liquids to form paints or in dry diluents to form powders.

The compound may be administered in conventional dosages as a single agent or in combination with a known, second therapeutically active compound.

For the methods of treatment disclosed herein, dosages can be varied depending upon the overall condition of the patient, the nature of the illness being treated and other factors. An example of a suitable dosage range is from about 0.1 to about 80 mg/kg per day, in single or divided doses. An example of a parenteral dosage regimen is from about 0.1 to about 80 mg/kg per day, in single or divided dosages, administered orally or by injection. An example of a topical dosage regimen is from about 0.1 mg to about 150 mg, administered from about one to four times a day. An example of an inhalation dosage regimen is from about 0.01 mg/kg to about 1 mg/kg per day.

Anti-cancer activity can be demonstrated in accordance with the following protocol.

Raf Kinase Assay

Raf kinase activity in vitro is measured by the phosphorylation of its physiological substrate MEK (Map kinase/ERK kinase). Phosphorylated MEK is subsequently trapped on a filter membrane and incorporation of radio-labeled phosphate is quantitated by scintillation counting.

MATERIALS

Activated Raf

Produced in Sf9 insect cells coinfected with three different baculoviruses expressing epitope-tagged Raf, and the upstream activators $Val^{12}$-H-Ras, and Lck. The epitope sequence Glu-Tyr-Met-Pro-Met-Glu ("Glu-Glu") was fused to the carboxy-terminus of full-length c-Raf.

MEK

Catalytically inactive MEK is produced in Sf9 cells infected with baculovirus expressing epitope-tagged MEK with a $lysine^{97}$ to alanine mutation (K97A). The epitope sequence Glu-Tyr-Met-Pro-Met-Glu ("Glu-Glu") was fused to the amino-terminus of full-length MEK1.

Anti "Glu-Glu" Antibody

A hybridoma cell line expressing an antibody specific for the "Glu-Glu" epitope was obtained from Gernot Walter, UCSD. Cells were grown and antibodies were purified as described (Grussenmeyer et al., Proc. Natl. Acad. Sci. U.S.A., 82, pp. 7952–7954, 1985).

Column Buffer 20 mM Tris, pH 8, 100 mM NaCl, 1 mM EDTA, 2.5 mM EGTA, 10 mM $MgCl_2$, 2 mM DTT, 0.4 mM AEBSF, 0.1% n-octyl glucopyranoside, 1 nM okadeic acid, and 10 μg/ml each of benzamidine, leupeptin, pepstatin, and aprotinin (all SIGMA).

5x Reaction Buffer 125 mM HEPES pH=8.0, 25 mM $MgCl_2$, 5 mM EDTA, 5 mM $Na_3VO_4$, 100 μg/ml BSA.

Enzyme Dilution Buffer 25 mM HEPES pH=8.0, 1 mM EDTA, 1 mM $Na_3VO_4$, 400 μg/ml BSA.

Stop Solution 100 mM EDTA, 80 mM sodium pyrophosphate.

Filter Plates

Millipore Multiscreen #SE3M078E3, Immobilon-P (PVDF).

METHOD

A. Protein Purification

1. Sf9 insect cells were infected with baculovirus and grown as described (Williams et al., Proc. Natl. Acad. Sci. U.S.A., 89, pp. 2922–2926, 1992).

2. All subsequent steps were performed on ice or at 4° C. Cells were pelleted and lysed by sonication in column buffer. Lysates were spun at 17,000x g for 20 min, followed by 0.22 μm filtration.

3. Epitope-tagged proteins were purified by chromatography over a GammaBind Plus (Pharmacia) affinity column to which "Glu-Glu" antibody had been coupled. Proteins were loaded on the column, followed by washes with two column volumes of column buffer, and eluted with 50 μg/ml of peptide antigen (Glu-Tyr-Met-Pro-Met-Glu) in column buffer.

B. Raf Kinase Assay

1. Add 10 μl of inhibitor or control in 10% DMSO to assay plate.

2. Add 30 μl of reaction mix containing 10 μl 5x reaction buffer and 0.5 μl 1 mM $^{33}$P-γ-ATP (20 μCi/ml), 0.5 μl MEK (2.5 mg/ml), 1 μl 50 mM β-mercaptoethanol.

3. Start reaction by addition of 10 μl enzyme dilution buffer containing 1 mM DTT and an empirically determined amount of activated Raf that produces linear incorporation kinetics over the reaction time course.

4. Mix and incubate at room temperature for 90 min.

5. Stop reaction by addition of 50 μl stop solution.

6. Prewet filter plate with 70% ethanol and rinse with water.

7. Transfer 90 μl aliquots of stopped reaction to filter plate.

8. Aspirate and wash four times with 200 μl H₂O.

9. Add 50 μl scintillation cocktail, seal plate, and count in Packard TopCount scintillation counter.

Map Kinase Phosphorylation Assay

Inhibition of Raf kinase activity in intact cells is measured by determining the phosphorylation state of Map Kinase in TPA-stimulated C-33a human epithelial cells. Phosphorylated Map Kinase is detected by "Western" blot using an anti-phospho-Map Kinase antibody.

MATERIALS

C33a Human Epithelial Cells

The C33a cell line is obtained from the ATCC repository, catalog #H TB31, and is maintained in DMEM (Mediatech)+10% fetal bovine serum+1% penicillin/streptomycin (Gibco) according to the instructions provided.

Anti-phospho-MAP Kinase Antibody

The rabbit polyclonal anti-phospho-MAP kinase antibody is obtained from New England Biolabs (Beverly, Mass.).

Secondary Antibody

The anti-rabbit antibody-alkaline phosphatase conjugate is obtained from New England Biolabs.

Acrylamide Gel

Ten percent bis-acrylamide electrophoresis gels were obtained from Novex.

Blocking Buffer

1x Phosphate-buffered saline, 0.1% Tween-20, 5% nonfat dry milk.

Antibody Dilution Buffer 1x phosphate-buffered saline, 0.05% Tween-20, 5% bovine serum albumin.

Alkaline Phosphatase Substrate

The chemiluminescent alkaline phosphatase substrate, CDP-Star™, is obtained from New England Biolabs.

Assay Buffer 0.1 M diethanolamine, 1 mM MgCl₂.

Method

1. C33a cells are grown to confluency in 24 well plates, then starved for 24 hr in DMEM+0.5% charcoal-stripped serum.

2. Compound to be tested, dissolved in DMSO at 1000x concentration, is added to each well.

3. One hour later, TPA (dissolved in DMSO at 1000x concentratrion) is added at a final concentration of 100 ng/ml.

4. Twenty minutes later, the media is removed from all wells, and 100 μl of boiling, hot reducing, Laemmli sample buffer is added to each well. The plate is agitated, and the cell lysate is transferred to a 1.5 ml plastic micro centrifuge tube. Each lysate is then sonicated for 10 s, and placed in a boiling, water bath for 5–10 minutes. Fifteen microliters of each sample is then loaded on a 10% Laemmli polyacrylamide gel (Novex), and the gel electrophoresed according to the manufacturer's instructions.

5. Proteins in the gel are electroblotted to a PVDF membrane, which is then rinsed in PBS and blocked with Blocking Buffer for approximately 1 hr at room temperature.

6. The PVDF membrane is rinsed in PBS. The anti-phospho-MapK antibody, diluted approximately 1:500 in antibody dilution buffer, is incubated with the PVDF membrane with gentle agitation overnight at 4° C.

7. The PVDF membrane is rinsed 3 times for 5 minutes with Blocking Buffer, then incubated with the secondary antibody, diluted approximately 1:1000 in antibody dilution buffer, for 1 hr with gentle agitation at room temperature.

8. The PVDF membrane is rinsed 5 times for 5 minutes with Blocking Buffer, then incubated with the chemiluminescent alkaline phosphatase substrate dissolved in Assay Buffer for approximately 5 minutes. The membrane is then rinsed, wrapped in plastic, and exposed to x-ray film to detect blotted proteins.

Certain preferred embodiments are described herein in detail. However, numberous alternative embodiments are contemplated as being within the scope of the invention described herein.

What is claimed is:

1. A compound represented by the formula I:

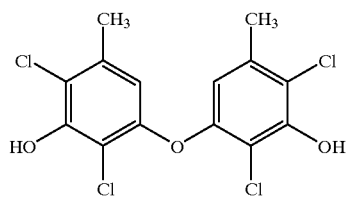

or a salt or hydrate thereof.

2. A pharmaceutical composition comprised of a compound in accordance with claim 1 in combination with a carrier.

3. A method of treating cancer in a mammalian patient in need of such treatment comprising admininstering to said patient an anti-cancer effective amount of a compound in accordance with claim 1.

4. A method in accordance with claim 3 wherein the cancer is a Raf mediated cancer.

5. A method in accordance with claim 3 wherein the cancer is selected from cancers of the brain, genitourinary tract, lymphatic system, stomach, larynx, and lung.

6. A process for producing a pharmaceutical composition containing a compound as described in claim 1, comprising combining a compound of formula I or a salt or hydrate thereof with a carrier therefore.

* * * * *